United States Patent
Nakatani et al.

(10) Patent No.: US 7,320,757 B2
(45) Date of Patent: Jan. 22, 2008

(54) BODY FLUID PROCESSOR ENABLING DIRECT HEMOPERFUSION

(75) Inventors: Masaru Nakatani, Settsu (JP); Akira Kobayashi, Settsu (JP); Shigeo Furuyoshi, Settsu (JP)

(73) Assignee: Kaneka Corporation, Osaka (JP)

( * ) Notice: Subject to any disclaimer, the term of this patent is extended or adjusted under 35 U.S.C. 154(b) by 366 days.

(21) Appl. No.: 10/250,367

(22) PCT Filed: Jan. 30, 2002

(86) PCT No.: PCT/JP02/00683

§ 371 (c)(1),
(2), (4) Date: Oct. 10, 2003

(87) PCT Pub. No.: WO02/060512

PCT Pub. Date: Aug. 8, 2002

(65) Prior Publication Data
US 2004/0222144 A1 Nov. 11, 2004

(30) Foreign Application Priority Data
Jan. 30, 2001 (JP) ............................ 2001-021480

(51) Int. Cl.
*B01D 15/00* (2006.01)
*B01D 24/10* (2006.01)
(52) U.S. Cl. ..................................... 210/666; 210/287
(58) Field of Classification Search ................ 210/266, 210/287
See application file for complete search history.

(56) References Cited

U.S. PATENT DOCUMENTS

| 2,682,268 A | * | 6/1954 | Ryan et al. .................... 422/44 |
| 4,261,828 A | * | 4/1981 | Brunner et al. ............. 210/287 |
| 4,409,105 A | * | 10/1983 | Hayashi et al. ............. 210/679 |
| 4,432,871 A | * | 2/1984 | Yamawaki et al. ...... 210/195.1 |
| 6,878,269 B2 | * | 4/2005 | Nanko et al. ................ 210/259 |

FOREIGN PATENT DOCUMENTS

| JP | 61-11620 B2 | 4/1986 |
| JP | 63-115572 A | 5/1988 |
| JP | 3-242300 A | 10/1991 |
| JP | 10-5329 A | 1/1998 |

* cited by examiner

*Primary Examiner*—Peter A. Hruskoci
(74) *Attorney, Agent, or Firm*—Sughrue Mion Pllc.

(57) ABSTRACT

A safe and practically useful body fluid processor whereby blood taken out from a patient can be directly processed, characterized by having a favorable passage of the blood cell and showing an extremely low risk of the generation and leakage of microparticles. Namely, a body fluid processor enabling direct hemoperfusion wherein the ratio of sedimented particles to the volume of the space in which the particles for processing body fluid are to be packed is 100% or less and the space in which the particles for processing body fluid are to be packed in the body fluid processor is filled with the particles for processing body fluid and a filling liquid at a ratio of 95% or more but not more than 100%.

4 Claims, 2 Drawing Sheets

BODY FLUID PROCESSOR ENABLING DIRECT HEMOPERFUSION

TECHNICAL FIELD

The present invention relates to a body fluid processor enabling direct processing of the blood in the extracorporeal circulation therapy where the blood taken out from a patient is processed to reduce the concentrations of disease-related substances and then returned to the patient and more particularly to a safe and practically useful body fluid processor having a favorable passage of the blood cell and showing an extremely low risk of leakage of microparticles.

BACKGROUND ART

In diseases resulting from accumulation of disease-related factors in blood, particularly in cases where the administration of drugs, for instance, is not sufficiently successful, blood purification by extracorporeal circulation (extracorporeal circulation treatment) is used as an effective therapeutic approach. Extracorporeal circulation treatment is a method of treatment which comprises taking out blood from the body, modifying it in some way or other to remove or ameliorate the disease-related factors such as the causative substances accumulated in the blood, abnormal cells, etc., and returning the blood so modified to the patient.

In the conventional extracorporeal circulation treatment where targets of removal are substances of low molecular weight, the removal by hemodialysis, hemofiltration or hemodialysis-filtration is efficient and has been exploited successfully for removal of the waste substances accumulated in the blood of a patient with a disease of the kidney (renal failure), for instance. For those cases in which the targets of removal are substances having high molecular weights which cannot be removed by hemodialysis or the like, many protocols have been developed and are in routine use for the blood purification by hemoperfusion which comprises separating plasma from blood with a plasma separating membrane or the like in advance and processing the plasma with a body fluid processor. For reducing the concentration of the causative substance present in plasma, several methods inclusive of adsorption, separation with a membrane, and separation by precipitation are known.

As a specific system for extracoporeal circulation treatment in which an adsorbent is used to remove causative substances from plasma, there is a system wherein the adsorbent is packed in a vessel equipped with an inlet and an outlet, the plasma is caused to flow directly into the vessel, and the plasma flowing out is returned to the patient (on-line system) or a system wherein the plasma is transferred to a blood bag or the like filled with the adsorbent in advance and, after mixing, the plasma, recovered by filtering off the adsorbent, is returned to the patient (batch system). From the standpoint of easy handling, the on-line system is used with preference.

Meanwhile, as an extracorporeal circulation treatment utilizing the particles for processing body fluid, a system in which the plasma is not separated from the blood but the blood is directly exposed to the particles for processing body fluid is attracting attention of late for its easy handling. The on-line system in which the blood is directly processed is called the direct hemoperfusion system. In this direct hemoperfusion system, it is necessary that the blood cells may pass through clearances between the particles for processing body fluid in a stable manner and there should be substantially no leakage of foreign matter, such as microparticles, from the body fluid processor. In addition, it must be insured that the blood can be efficiently processed to complete the treatment in a short time not imposing appreciable burdens on the patient and medical staff. However, this is technically not easily feasible.

One of the important factors enabling a stable direct hemoperfusion is the diameter of the particles for processing body fluid. Generally the efficiency of body fluid processing can be improved by reducing the mean particle diameter and increasing the effective surface area of the particles for processing body fluid to be used but if the particle diameter is excessively decreased, the clearance between particles is diminished to interfere with passage of the blood cells so that a stable direct hemoperfurion becomes difficult.

Researches have heretofore been undertaken on the particles for processing body fluid suitable for direct hemoperfusion systems in the aspect of physical and chemical characteristics of the particles for processing body fluid. Japanese Kokai Publication Sho-63-115572, with attention directed to the mean particle diameter and particle size distribution, discloses that the particles so engineered that "the volume mean particle diameter is 80 to 400 µm, that particles accounting for not less than 80 volume % are distributed within ±20% of the volume mean particle diameter, and that the percentage of particles smaller than 74 µm in diameter is not less than 5 volume % while that of particles smaller than 25 µm in diameter is not more than 0.1 volume %", can be utilized as beads enabling direct hemoperfusion. Japanese Kokai Publication Hei-10-005329 describes that "when a sulfated polysaccharide and/or a salt thereof is coupled to a water-insoluble carrier", the blood perfusion is improved and the mean particle diameter can be reduced as compared with the intact water-insoluble carrier.

For both of the above artifacts, their utility as the particles for processing body fluid has been studied but in order that these artifacts may be practically useful, it is not only essential that the artifacts as such be satisfactory enough as the particles for processing body fluid but also necessary that body fluid processors prepared by packing these artifacts display satisfactory characteristics.

The important point of any body fluid processor of the direct hemoperfusion type from the standpoint of practical utility is that it shows a favorable passage of the blood cells and the blood can be allowed to flow through it at as high a speed as possible in a stable manner. When these requirements are satisfied, an efficient therapy can be administered in a short session time not imposing any appreciable burden on the patient and medical staff.

The important point of a body fluid processor of the direct hemoperfusion type from safety viewpoints is a low risk of leakage of microparticles from the body fluid processor. When a large amount of microparticles exists in the body fluid processor, the microparticles tend to be carried away by blood from the body fluid processor and find their way into the patient's vascular system to clog the capillary blood vessels. Therefore, if only for the purpose of minimizing the risk of leakage of microparticles, it is ideal to provide a body fluid processor packed with the particles for processing body fluid having no potential of generation of microparticles in a microparticles-free condition. However, since porous particles are often used as the particles for processing body fluid in order that the body fluid processing may be accomplished with efficiency, it is technically difficult to provide the particles for processing body fluid which do not generate microparticles and hence it is virtually impossible to implement such an ideal body fluid processor. Therefore, it is of great importance to pack the particles for processing body fluid with the lowest possible potential of generation of microparticles in as microparticles-free condition as possible and in a manner protected against the generation of microparticles within the body fluid processor even when the processor is subjected to vibrations.

As a means for solving above problems, a method of controlling generation of microparticles is known as disclosed in Japanese Kokoku Publication Sho-61-11620 wherein the "adsorbent is pressed to securely fix it in a column" so that the particles for processing body fluid may not readily move within the body fluid processor. However, in the art described in this patent literature, it is not discussed or explored whether the device is useful as a body fluid processor enabling direct hemoperfusion, that is to say whether the blood can be directly passed through the device in a stable manner. In a body fluid processor of the direct hemoperfusion type, if the particles for processing body fluid are immobilized by pressing, it is likely that the clearance between particles is narrowed to interfere with the free flow of blood or the particles are destroyed by compressive forces to generate microparticles.

Conversely when the particles for processing body fluid are not held stationary but are free to move within the body fluid processor, it may happen that vibrations, for instance, cause collision of the particles for processing body fluid to generate microparticles.

Thus, no sufficient studies have heretofore been undertaken on the body fluid processor enabling direct hemoperfusion from safety and practical utility points of view.

SUMMARY OF THE INVENTION

In the above state of the art, the present invention provides a body fluid processor of direct hemoperfusion type which shows an extremely low risk of the generation and leakage of microparticles and permits blood perfusion at as high a flow rate as practicable and in a stable manner.

The inventors of the present invention did intensive studies on the correlation of the packed condition of the particles for processing body fluid and a filling liquid with the efficiency of blood perfusion and leakage of microparticles. As a consequence, they found that when the ratio of sedimented particles to the volume of the space in which the particles for processing body fluid are to be packed is 100% or less and the space in which the particles for processing body fluid are to be packed is filled with the particles for processing body fluid and a filling liquid at a ratio of 95% or more but not more than 100%, there can be obtained a body fluid processor of practical utility which has a favorable passage of the blood cell even at a high flow rate and shows an extremely low risk of the generation and leakage of microparticles. The present invention has accordingly been developed.

The present invention, therefore, is directed to
a body fluid processor enabling direct hemoperfusion,
which comprises a vessel equipped with a fluid inlet, a fluid outlet and a mesh attached adjacent to said fluid outlet,
said vessel being packed with the particles for processing body fluid and a filling liquid,
the ratio of sedimented particles to the volume of the space in which the particles for processing body fluid are to be packed being 100% or less and
the space in which the particles for processing body fluid are to be packed in the body fluid processor being filled with the particles for processing body fluid and a filling liquid at a ratio of 95% or more but not more than 100%.

The present invention is further directed to
a body fluid processor enabling direct hemoperfusion,
wherein the mean particle diameter of the particles for processing body fluid is 80 µm through 500 µm;
a body fluid processor enabling direct hemoperfusion,
wherein the aperture size of the mesh is not less than 20 µm but less than ½ of the mean particle diameter of the particles for processing body fluid;
a body fluid processor enabling direct hemoperfusion,
wherein the particles for processing body fluid are hard particles;
a body fluid processor enabling direct hemoperfusion,
wherein the carrier for the particles for processing body fluid is a hydrophilic carrier;
and a body fluid processor enabling direct hemoperfusion,
wherein the carrier for the particles for processing body fluid is a carrier made of a cellulosic material.

DETAILED DESCRIPTION OF THE INVENTION

The vessel of the body fluid processor for use in the invention is equipped with a fluid inlet, a fluid outlet, and a mesh attached adjacent to said liquid outlet.

The constituent material of the vessel is not particularly restricted but may for example be polypropylene or polycarbonate.

The mesh to be used should be one that can be retained in position so as to preclude escape of the particles for processing body fluid from the body fluid processor and capable of allowing blood perfusion therethrough. The construction of the mesh may be any of an interlaced filament structure, a woven fabric, a flat apertured plate having a multiplicity of through-holes, a nonwoven fabric, a filter such as a cotton plug, and a bamboo blind-like structure, among others. The material of such a mesh is not particularly restricted but may for example be any of polyester, polyethylene, polypropylene, polyamide, and nylon.

While the through-holes of a mesh through which blood flows are referred to as apertures, it is to be understood that when the configuration of the aperture is circular, the diameter of the circle can be taken as the aperture size. In the case of a square configuration, the diameter of an equivalent circle of the same area can be used. When the aperture is a bamboo blind-like, the length on the side of shorter interval can be used.

To allow blood to flow through, the aperture size of the mesh is preferably not less than 20 µm. If it is less than this threshold, the blood cells are liable to be trapped by the meshes. However, in order that the leakage of the particles for processing body fluid may be prevented, the aperture size of the mesh is preferably less than ½ of the mean diameter of the particles for processing body fluid. The more preferred aperture size is not less than 30 µm but less than ⅖ of the mean diameter of the particles for processing body fluid. Particularly when there is a gradient in the particle size distribution, it is advisable to take particles smaller than the mean diameter into account and select an aperture size small enough to prevent leak-out of such smaller particles.

In addition, for preventing loss of the particles for processing body fluid from the body fluid processor through the fluid inlet, there may be attached a similar mesh adjacent to the fluid inlet.

In the body fluid processor of the invention, the ratio of sedimented particles to the volume of the space in which said particles are to be packed is 100% or less and the space in which the particles for processing body fluid are to be packed in the body fluid processor is filled with the particles for processing body fluid and a filling liquid at a ratio of 95% or more but not more than 100%.

For the convenience of description, the ratio of sedimented particles to the volume of the space in which the particles for processing body fluid are to be packed will hereinafter be referred to briefly as "packing ratio" and the ratio of the particles for processing body fluid and a filling liquid to the volume of the space in which the particles for processing body fluid in the body fluid processor are to be packed will be referred to briefly as "occupancy ratio".

The packing ratio in the context of the invention can be calculated by means of the following equation:

$$\text{Packing ratio (\%)} = Va/Vj \times 100$$

where Va represents the sedimentation volume of the particles for processing body fluid packed in the space in which the particles for processing body fluid are to be packed and Vj represents the volume of the space in which the particles for processing body fluid are to be packed.

In this connection, Va is determined as follows. Thus, the whole amount of the particles for processing body fluid packed in the space in which the particles for processing body fluid are to be packed is transferred, in the form of a slurry prepared by addition of water, to a measuring cylinder and the particles for processing body fluid in slurry form are allowed to settle spontaneously in the measuring cylinder. Then, this measuring cylinder is placed on a base such as a rubber mat resistant to the impact of a falling glassware and the measuring cylinder is dropped perpendicularly from a height of about 10 cm about 10 times. After allowing the cylinder to sit for not less than 15 minutes, the sedimentation volume of the particles for processing body fluid is read out and recorded. The above dropping and sitting procedure is repeated and the sedimentation volume of the particles for processing body fluid in the stage where there is no change in the volume any longer is recorded as Va.

The occupancy ratio in the present invention is calculated as follows. Thus, the whole amount of the particles for processing body fluid and a filling liquid packed in the space in which the particles for processing body fluid are to be packed is transferred, in the form of a slurry prepared by addition of water (volume: Vw), to a measuring cylinder. The volume (Vin) of this whole slurry is found by reading the scale of the cylinder. The occupancy ratio is calculated by means of the following equation.

$$\text{Occupancy ratio (\%)} = (Vin - Vw)/Vj \times 100$$

The state in which the occupancy ratio is 100% corresponds to the state in which the space to be packed with the particles for processing body fluid within the body fluid processor has been packed with the same volume of the particles for processing body fluid as the volume of said space, with the result that the particles for processing body fluid will not be easily displaced, nor will the particles for processing body fluid be deformed or compacted; thus it is an ideal state at low risk of the generation of microparticles due to vibrations, for instance. However, in the actual manufacturing of body fluid processors, it is impossible to invariably align the packing ratio of the particles for processing body fluid at 100% and, therefore, a variation is inevitable in the packing ratio of body fluid processors manufactured.

On the other hand, when the packing ratio is less than 100%, the particles for processing body fluid are not securely immobilized but are free to move within the body fluid processor so that it may happen that vibrations, for instance, cause collisions of the particles for processing body fluid and, hence, generation of microparticles. In other to reduce the possibility of flow-out of microparticles from the body fluid processor in the course of treatment, it is preferable that the number of microparticles in the body fluid processor should be as low as possible.

Under the circumstances, the inventors of the present invention did intensive studies and found that, when the packing ratio is not more than 100% and the occupancy ratio is 95% through 100%, the resulting body fluid processor enables direct hemoperfusion through which blood may flow in a practically acceptable manner while generation of microparticles is suppressed.

When the packing ratio exceeds 100%, the particles for processing body fluid are held stationary in the body fluid processor and cannot easily move so that it is not likely that vibrations, for instance, cause collisions of the particles for processing body fluid to generate microparticles. However, when blood is passed through a body fluid processor packed to a packing ratio in excess of 100%, the passage of the blood cells, particularly platelets, is unstable in many cases and there also are cases in which the pressure drop increases progressively to ultimately prevent the blood to flow through the processor. This is presumably because, in the case where the packing ratio exceeds 100%, the particles for processing body fluid are deformed and compressed as compared with the pre-packing state and when the deformation and compression are excessive, the clearances between particles are narrowed to adversely affect the efficiency of passage of the blood cells.

In contrast, in the case where the packing ratio is not higher than 100%, passage of the blood cell is efficient and the blood can be passed under the condition of stable pressure drop when blood flows. There is no particular lower limit of packing ratio but if the packing ratio is too low, the packing amount of the particles for processing body fluid is so low that the objective body fluid processing cannot be easily accomplished. Moreover, if the packing ratio is decreased, the blood processing efficiency is relatively sacrificed despite an increased amount of blood withdrawn from the body. Therefore, the packing ratio is preferably not less than 70%, more preferably not less than 85%, still more preferably not less than 90%, most preferably not less than 95%.

Further detailed analysis revealed that provided that the occupancy ratio is 95% through 100%, most preferably 98% through 100%, even when the packing ratio is less than 100%, that is to say when the particles for processing body fluid are not held stationary but are free to move, and for that matter, 100%, the number of microparticles in the body fluid processor after vibrations is remarkably low. Furthermore, when physiological saline instead of blood was passed and the microparticles migrating from the body fluid processor was counted, substantially no microparticles could be detected, indicating that a body fluid processor with a drastically reduced risk of leakage of microparticles can be provided.

The particles for processing body fluid to be used in the present invention are solid at atmospheric temperature and pressure and water-insoluble.

The morphology of the particles for processing body fluid for use in the invention is generally spherical, with the mean particle diameter being preferably not less than 80 µm. If the mean particle diameter is too small, the inter-particle clearances are so narrow that the passage of the blood cells is liable to be interfere with. There is no critical upper limit of mean particle diameter but an increasing mean particle diameter results in a decreasing surface area of the particles for processing body fluid and, hence, a decreasing body fluid processing efficiency. Therefore, the mean particle diameter is preferably not more than 500 µm. The more preferred range of mean particle diameter is 120 µm to 300 µm.

Regarding the particle size distribution of the particles for processing body fluid according to the invention, all particles may be uniform in diameter or particles varying in diameter may co-exist presenting the so-called distribution in particle diameter. However, if the particle size distribution is too broad, it may mean that many small particles are present although the mean particle diameter is constant so that the inter-particle clearances are locally narrowed to obstruct passage of the blood cells. Therefore, the particle size distribution is preferably as narrow as possible. More preferably, 50% or more of particles have diameters within ±20% of the mean diameter and still more preferably 60% or more of particles have diameters within ±20% of the mean diameter.

With regard to the strength of the particles for processing body fluid for use in the invention, particles which are too soft or easily collapsible are undesirable. The compaction resulting from blood perfusion would make it impossible to secure a sufficient blood flow rate and, therefore, prolong the treatment time or even prevent continuation of the treatment. To prevent this compaction of the particles for processing body fluid, it is desirable to employ the particles for processing body fluid having sufficiently high mechanical strength (hardness). The hardness referred to above means that when a cylindrical column is uniformly packed with the particles for processing body fluid and an aqueous fluid is admitted into the column, the relation of pressure drop and flow rate is linear at least until the pressure drop has reached 0.3 kgf/cm$^2$ (ca 220 mmHg) as will be explained hereinafter in reference examples.

The particles for processing body fluid for use in the invention preferably has a porous structure having a multiplicity of pores of adequate size in consideration of the efficiency of body fluid treatment. The porous structure mentioned above is not only relevant to a solid substance having micropores defined by clusters of microspheres as occurring when a fundamental polymer carrier forms a single spherical particle due to cohesion of microspheres but also relevant to a solid substance having micropores formed by and among clusters of nuclei within the individual microspheres constituting a fundamental polymer carrier or the micropores which form when a copolymer having a three-dimensional structure (a polymer network) is swollen by an organic solvent which has an affinity for the copolymer.

The constituent material of the carrier for the particles for processing body fluid according to the invention is not particularly restricted but includes such representative materials as organic carriers composed of polysaccharides such as cellulose and its derivatives, dextrin and so forth and synthetic polymers such as polystyrene, polyacrylamide, polyacrylate esters, polymethacrylate esters, polyvinyl alcohol, saponified poly(ethylene-co-vinyl acetate) and so forth. Moreover, for suppressing the formation of microparticles and facilitating the passage of the blood cells, the surface of the particles for processing body fluid is preferably as smooth as possible.

Among the carrier materials mentioned above, hydrophilic carriers are preferred because non-specific adsorption is small. The term 'hydrophilic carrier' is used in this specification to mean a carrier such that when the compound constituting it is formed into a flat board, its angle of contact with water is not larger than 60 degrees. Such carriers typically include cellulose and its derivatives, poly(vinyl alcohol), saponified poly(ethylene-co-vinyl acetate), and polyacrylamide carriers, although these are not exclusive choices.

Among these, cellulosic carriers are most advantageous. Cellulosic carriers have many meritorious characteristics such as (1) comparatively high mechanical strength and toughness with a minimum risk of the collapse and the generation of microparticles, and high resistance to compaction in a column even under the high-rate flow of blood, thus allowing blood to be passed at a high flow rate and (2) high safety as compared with synthetic polymer carriers. Thus, these carriers can be used with the greatest advantage for the particles for processing body fluid according to the invention.

In the context of the present invention, the term "cellulosic" is used referring to at least one of natural cellulose, regenerated cellulose, and cellulose derivatives. Natural cellulose, for instance, includes defatted cotton fiber, linen, pulp made by removing lignin, hemicellulose and so forth from wood, and purified cellulose obtainable by further purification of said pulp, among others. Regenerated cellulose is a cellulose obtained by derivatizing natural cellulose into a cellulose derivative and regenerating it by, for example, hydrolysis. The cellulose derivative includes derivatives of natural or regenerated cellulose as obtained by partial or total esterification and/or etherification of its hydroxyl groups, among others. Specifically, the derivative of a cellulose obtained by partial or total esterification of its hydroxyl groups includes but is not limited to cellulose acetate, cellulose propionate, cellulose butyrate, nitrocellulose, cellulose sulfate, cellulose phosphate, cellulose acetate butyrate, cellulose nitrate, and dicarboxlic esters of cellulose. The cellulose derivative obtained by partial or total etherification of its hydroxyl groups includes but is not limited to methylcellulose, ethylcellulose, benzylcellulose, cyanoethylcellulose, carboxymethylcellulose, aminoethylcellulose, and hydroxyethylcellulose.

While any of these carriers may be used, as it is, as the particles for processing body fluid, any of such carriers may be conjugated or otherwise coupled with the so-called ligand and used as the particles for processing body fluid. The ligand that can be immobilized includes but is not limited to amino acids such as phenylalanine, tryptophan, etc., polylysine, diethylaminoethyl-compounds and other positively charged compounds, polyacrylic acid, dextran sulfate and other negatively charged compounds, n-hexadecylamine and other hydrophobic compounds, polymyxin and other antibiotics, antibodies against accumulated disease-related factors or partial peptides of such antibodies.

The filling liquid for use in the invention includes water, electrolyte solutions (physiological saline, sodium citrate solution, etc.), buffer solutions for maintaining pH constant (citric acid-sodium citrate buffer, citric acid-sodium hydroxide buffer, citric acid-disodium hydrogenphosphate buffer, phosphate buffer, etc.), antioxidant solutions for preventing degradation of the particles for processing body fluid (sodium sulfite-containing aqueous solution, sodium pyrosulfite-containing aqueous solution, L-ascorbic acid-containing aqueous solution, DL-α-tocopherol-containing aqueous solution, etc.) among others, and these can be selectively used according to characteristics of the particles for processing body fluid.

The capacity of the body fluid processor and the flow rate of blood, among other variables, can be judiciously selected depending on the therapeutic goal and the patient's condition. Generally speaking, the capacity of the body fluid processor may be 100 to 1000 ml and the flow rate of blood to be treated is not more than 200 ml/min. In cases where the patient's body weight is heavy and/or the concentration of the disease-related factor to be depressed is high, the absolute amount of the disease-related factor whose level is to be depressed is so large that the body fluid processor is also required to have a large capacity. An extracorporeal circulation treatment may be performed using a body fluid processor of large capacity, of course, but for the purpose of lessening the burden on the patient, for instance, it may be a reasonable approach to somewhat reduce the concentration of the disease-related factor using a body fluid processor, then either replace the used processor with an unused one or regenerate the used one to restore its potency to reduce the concentration of the disease-related factor, and perform an additional session of extracorporeal circulation treatment.

The anticoagulant which can be used in such an extracorporeal circulation treatment with the body fluid processor according to the invention includes heparin, low-molecular-weight heparin, nafamostat mesylate, gabexate mesylate, argatroban, citric acid-containing anticoagulants such as acid-citrate-dextrose (ACD) solution and citrate-phosphate-dextrose (CPD) solution, and any of these can be employed. Above all else, citric acid-containing anticoagulants, namely ACD-A solution and CPD-A solution, are used as advantageous anticoagulants because these agents chelate the calcium ions in blood to exhibit strong anticoagulant actions.

An example of the extracorporeal circulation system using the body fluid processor of the invention is now described. A blood collecting circuit for guiding the blood drawn from the patient's body to the body fluid processor is connected to the fluid inlet of the processor, while a blood return circuit for returning the blood cleared of the causative factor by adsorption to the patient's body is connected to the fluid outlet of the processor. Then, a pump is set for delivery of the blood to the blood collecting circuit. Moreover, an air chamber is connected to a manometer to measure the fluid inlet pressure and fluid outlet pressure of the body fluid processor, whereby the pressure drop of the body fluid processor can be determined. In practical treatment, the blood withdrawn from the patient's body is treated with a suitable anticoagulant and delivered to the body fluid processor in which the concentration of the disease-related factor is lowered and the blood so treated is returned to the patient's body.

Figure 1:
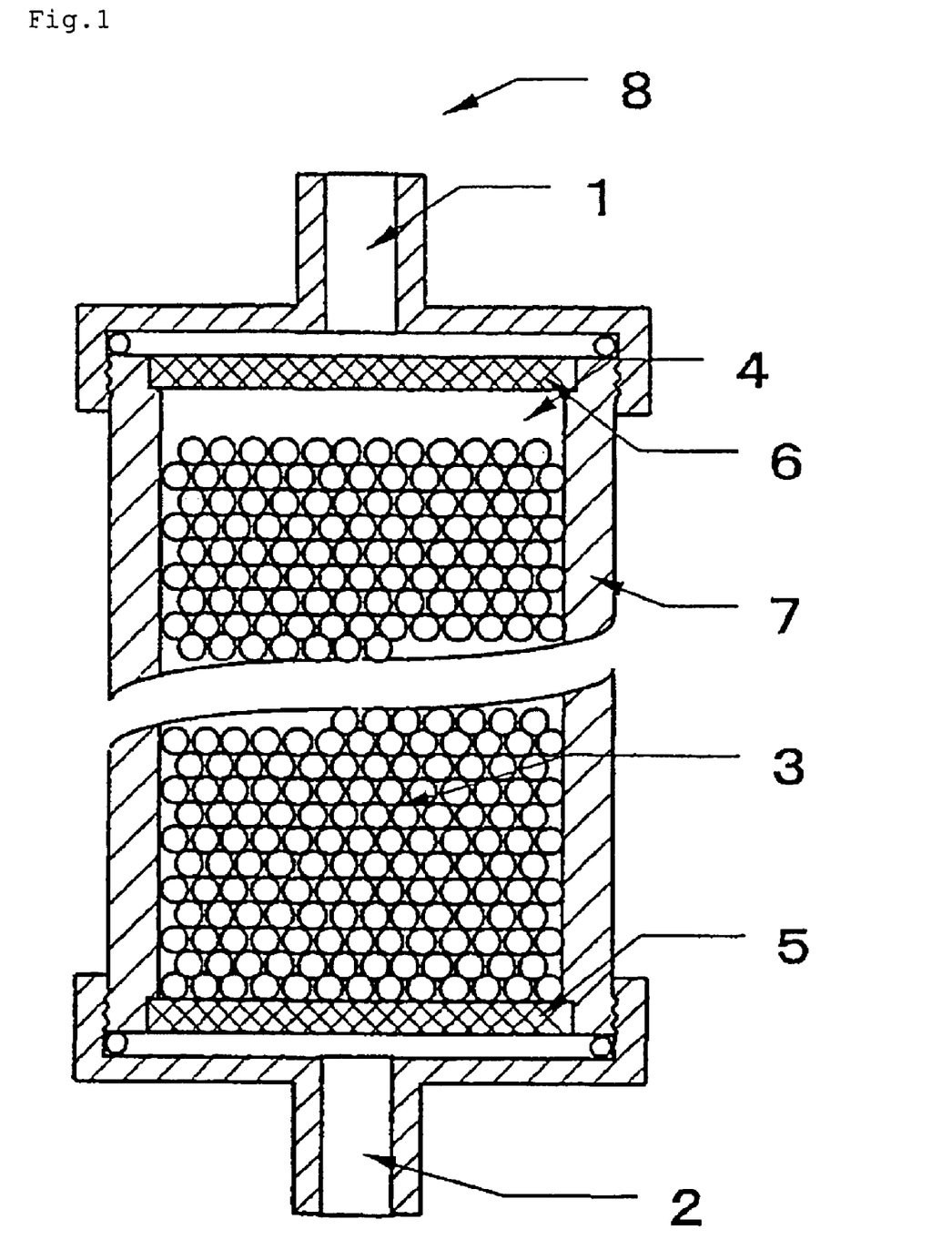
FIG. 1 is a schematic cross-section view showing an example of the body fluid processor according to the invention.

The body fluid processor of the invention is now described in detail referring to FIG. 1 which shows an example of the processor in schematic cross-section. In FIG. 1, the reference numeral 1 indicates a body fluid inlet, 2 a body fluid outlet, 3 the particles for processing body fluid, 4 a filling liquid, 5 and 6 each a mesh, 7 a column, and 8 a body fluid processor. It should, however, be understood that the body fluid processor according to the invention is not limited to the above specific embodiment but may virtually be any processor comprising a vessel equipped with a fluid inlet, a fluid outlet, and meshes for preventing the particles for processing body fluid from leaking out from the vessel packed with the particles for processing body fluid.

BEST MODES FOR CARRYING OUT THE INVENTION

The method of the invention is now specifically described by way of examples but is by no means restricted to these specific examples.

REFERENCE EXAMPLE

A glass cylindrical column (9 mm in. dia., 150 mm long) fitted with a filter (15 μm aperture dia.) at either end was uniformly packed with an agarose material (product of Bio-rad, Biogel A-5m, particle size: 50 to 100 mesh), a polyvinyl resin material (product of Tosoh Corporation, Toyopearl HW-65, particle size: 50 to 100 μm), and a cellulosic material (product of Chisso Corporation, Cellulofine GC-700 m, particle size: 45 to 105 μm). Then, water was admitted into the column with a peristaltic pump to determine the relation between flow rate and pressure drop ΔP. The results are shown in FIG. 2.

Figure 2:
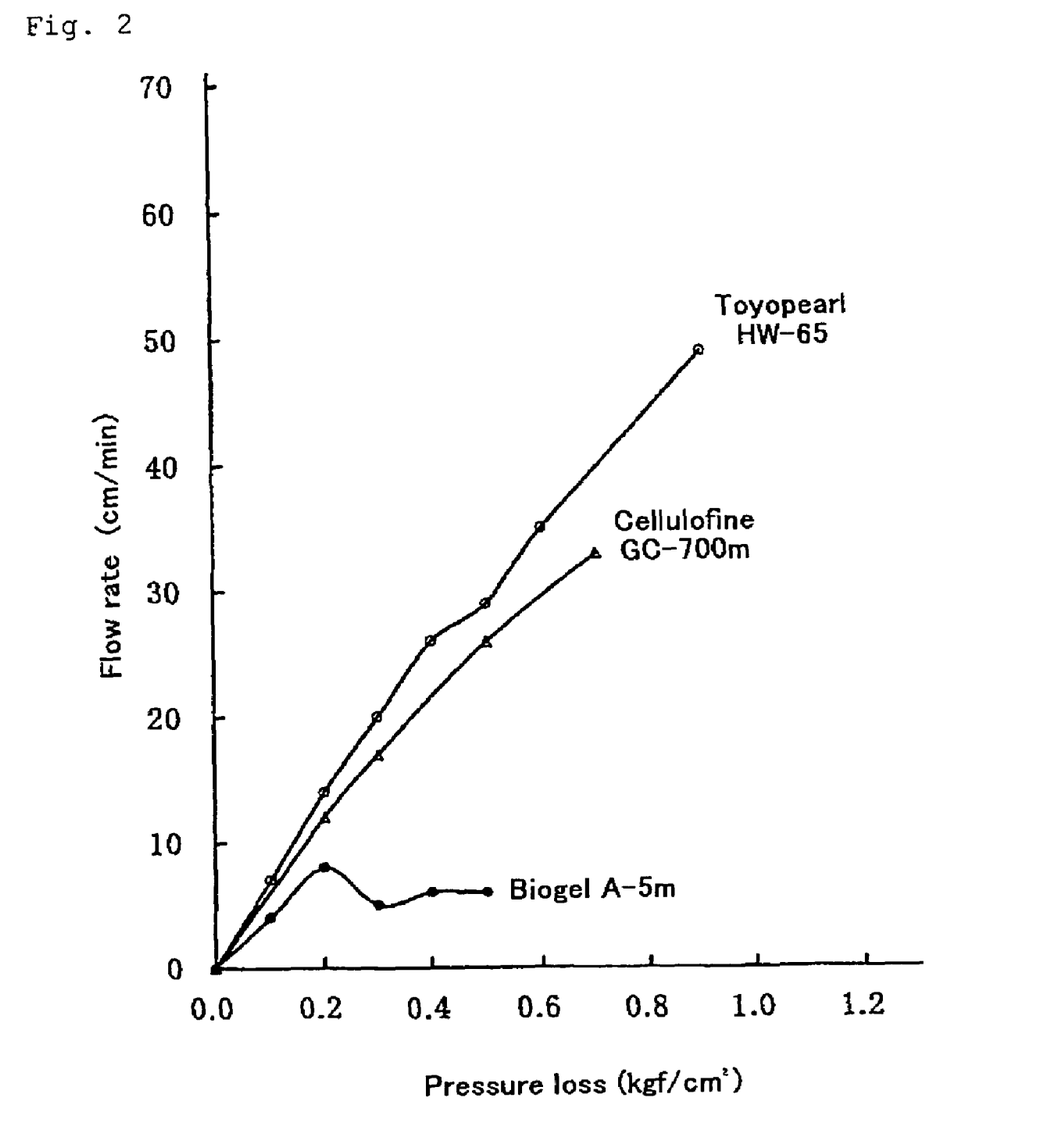
FIG. 2 is a graph showing the relation between flow rate and pressure drop as found when a cylindrical column is uniformly packed with the necessary materials and water is passed through the column.

It can be seen from FIG. 2 that whereas the flow rate increased generally in proportion with the increase in pressure drop in the case of Toyopearl HW-65 and Cellulofine GC-700m, Biogel A-5m was compacted so that the flow rate failed to increase even when the pressure drop was increased. In the present invention, any material showing a linear relation between pressure drop ΔP and flow rate at least until the pressure drop has reached 0.3 kgf/cm$^2$ (ca 220 mmHg), as it is true of the former materials, is regarded as being hard.

Example 1

To 2000 ml of porous cellulose beads with a mean particle diameter of about 190 μm (product of Chisso Corporation) were added 2000 ml of water, 1060 ml of 2 N aqueous solution of NaOH, and 360 ml of chloromethyloxysilane, and the mixture was stirred at 40° C. for 2 hours. After completion of the reaction, the beads were rinsed thoroughly with water to give epoxy-activated cellulose beads.

In 630 ml of water was dissolved 930 g of dextran sulfate (product of Meito Sangyo Co., sulfur content ca 18%) to prepare an aqueous solution of dextran sulfate and 2000 ml of the epoxy-activated cellulose beads and 100 ml of water were added to the solution. After the mixture was adjusted to pH 9.5 with an aqueous solution of NaOH, the reaction was carried out at 45° C. for 22 hours. After this reaction, the beads were thoroughly washed with water and aqueous solution of NaCl and following addition of 19.6 ml of 2-aminoethanol, the mixture was allowed to stand at 45° C. for 2 hours to block the unreacted epoxy groups. Thereafter, the beads were thoroughly rinsed with water to give dextran sulfate-immobilized cellulose beads (the particles for processing body fluid).

Of the above the particles for processing body fluid, 138 ml in sedimentation volume was taken and packed into a 3.1 cm (in. dia.) cylindrical vessel (the volume of packed zone: ca 142 ml) equipped with two 50 μm-apertured polyester meshes rigidly mounted at a mesh-to-mesh distance of 18.8 cm to prepare a body fluid processor with a packing ratio of ca 97% and an occupancy ratio of ca 100%. Physiological saline was used as a filling liquid.

Using 1200 ml of bovine blood (ionized Ca concentration: ca 0.45 mM), which has been subjected to anticoagulation by citric acid, as a blood pool, the blood was circulated through the above body fluid processor at a flow rate of 20 ml/min (superficial linear velocity: ca 2.6 cm/min) (the time of circulation start was designated as min-O). As a result, a stabilized passage of the blood cell was obtained over min-O to min-90. During this time the pressure drop of the body fluid processor was stable around 70 mmHg. During the subsequent period of min-90 to min-95, increasing the flow rate to 29 ml/min (superficial linear velocity: ca 3.9 cm/min) resulted in a stable blood perfusion with the pressure drop of the body fluid processor being stable around 110 mmHg. During the period of min-95 to min-100, increasing the flow rate to 39 ml/min (superficial linear velocity: ca 5.2 cm/min) resulted in a stable blood perfusion with the pressure drop of the body fluid processor being stable around 160 mmHg. Then, during min-100 to min-105, increasing the flow rate to 49 ml/min (superficial linear velocity: ca 6.5 cm/min) resulted in a stable blood perfusion with the pressure drop of the body fluid processor being stable around 210 mmHg. The passage ratio of blood cells was also satisfactory. The passage ratios of various blood cells were shown in Table 1.

The passage ratios of various blood cells were determined by sampling the blood serially at the inlet and outlet of the body fluid processor, counting the cells with a blood cell counter (manufactured by Sysmex Corporation, K-4500), and calculating the ratio by means of the following equation.

Passage ratio of blood cells=the number of blood cells at fluid outlet of the body fluid processor/ the number of blood cells at fluid inlet of the body fluid processor Example 2

Of the particles for processing body fluid prepared in Example 1, 142 ml in sedimentation volume was taken and packed into a vessel similar to the one used in Example 1 to prepare a body fluid processor with a packing ratio of ca 100% and an occupancy ratio of ca 100%. Physiological saline was used as a filling liquid.

Using 1200 ml of bovine blood (ionized Ca concentration: ca 0.6 mM), which has been subjected to anticoagulation by citric acid, as a blood pool, the blood was circulated through the body fluid processor at a flow rate of 20 ml/min (superficial linear velocity: ca 2.6 cm/min) (the time of circulation start was designated as min-0). As a result, a stabilized passage of the blood cell was obtained over min-O to min-90. During this time the pressure drop of the body fluid processor was stable around 90 mmHg. During the subsequent period of min-90 to min-95, increasing the flow rate to 29 ml/min (superficial linear velocity: ca 3.9 cm/min) resulted in a stable blood perfusion with the pressure drop of the body fluid processor being stable around 130 mmHg. During the period of min-95 to min-100, increasing the flow rate to 39 ml/min (superficial linear velocity: ca 5.2 cm/min) resulted in a stable blood perfusion with the pressure drop of the body fluid processor being stable around 190 mmHg. Furthermore, during the period of min-100 to min-105, increasing the flow rate to 49 ml/min (superficial linear velocity: ca 6.5 cm/min) resulted in a stable blood perfusion with the pressure drop of the body fluid processor being stable around 250 mmHg. The passage ratio of blood cells was also satisfactory. The passage ratios of various blood cells were shown in Table 1.

Example 3

Of the particles for processing body fluid prepared in Example 1, 708 ml in sedimentation volume was taken and packed into a 7.0 cm (in. dia.) cylindrical vessel (the volume of packed zone: ca 730 ml) equipped with two 48 μm-apertured polyester meshes rigidly mounted at a mesh-to-mesh distance of 19 cm to prepare a body fluid processor with a packing ratio of ca 97% and an occupancy ratio of ca 100%. Citric acid-sodium citrate buffer (pH=6.0) was used as a filling liquid.

The body fluid processor was washed with 2000 ml of physiological saline and using 7000 ml of bovine blood (ionized Ca concentration: ca 0.5 mM), which has been subjected to anticoagulation by citric acid, as a blood pool, the blood was circulated through the body fluid processor at a flow rate of 100 ml/min (superficial linear velocity: ca 2.6 cm/min) (the time of circulation start was designated as min-0). As a result, a stabilized passage of the blood cell was obtained over min-O to min-90. During this time the pressure drop of the body fluid processor was stable around 70 mmHg. During the subsequent period of min-90 to min-95, increasing the flow rate to 150 ml/min (superficial linear velocity: ca 3.9 cm/min) resulted in a stable blood perfusion with the pressure drop of the body fluid processor being around 110 mmHg. During the period of min-95 to min-100, increasing the flow rate to 200 ml/min (superficial linear velocity: ca 5.2 cm/min) resulted in a stable blood perfusion with the pressure drop of the body fluid processor being stable around 160 mmHg. The passage ratio of blood cells was also satisfactory. The passage ratios of various blood cells were shown in Table 1.

Comparative Example 1

Of the particles for processing body fluid prepared in Example 1, 146 ml in sedimentation volume was taken and packed into a vessel similar to the one used in Example 1 to prepare a body fluid processor with a packing ratio of ca 103% and an occupancy ratio of more than 100%. Physiological saline was used as a filling liquid.

Using 1200 ml of bovine blood (ionized Ca concentration: ca 0.6 mM), which has been subjected to anticoagulation by citric acid, as a blood pool, the blood was circulated through the body fluid processor at a flow rate of 20 ml/min (superficial linear velocity: ca 2.6 cm/min). As a result, a stabilized passage of the blood cell was achieved with a pressure drop of ca 90 mmHg up to around min-75 but subsequently a gradual gain in pressure drop was noted, with the pressure drop being as high as ca 120 mmHg at min-90. The passage ratio of blood cells declined with time. The passage ratios of various blood cells were shown in Table 1.

Comparative Example 2

Using porous cellulose beads with a mean particle diameter of ca 210 μm, the procedure described in Example 1 was otherwise repeated to give dextran sulfate-immobilized cellulose beads (the particles for processing body fluid). Of the particles for processing body fluid, 781 ml in sedimentation volume was taken and packed into a vessel similar to the one used in Example 3 to prepare a body fluid processor with a packing ratio of ca 107% and an occupancy ratio of more than 100%. Physiological saline was used as a filling liquid.

Using 7000 ml of bovine blood (ionized Ca concentration: ca 0.45 mM), which has been subjected to anticoagulation by citric acid, as a blood pool just as in Example 3, the blood was circulated through the body fluid processor at a flow rate of 100 ml/min (superficial linear velocity: ca 2.6 cm/min). The blood could be passed in a stable manner with the pressure drop being stable around 100 mmHg during an initial phase of treatment but the pressure drop increased sharply about 30 minutes after the start of circulation. After about 40 minutes, the pressure drop reached about 350 mmHg due to compaction of the particles for processing body fluid, preventing circulation of blood. The passage ratio of blood cells, especially the passage ratio of platelets, was extremely low. The passage ratios of various blood cells were shown in Table 1.

Example 4

Of the particles for processing body fluid prepared in Example 1, 13.4 ml in sedimentation volume was taken and packed into a 1 cm (in. dia.) cylindrical vessel (the volume of packed zone: ca 14.9 ml) equipped with two 50 μm-apertured polyester meshes rigidly mounted at a mesh-to-mesh distance of 19 cm to prepare a body fluid processor with a packing ratio of ca 90% and an occupancy ratio of ca 100%. Citric acid-sodium citrate buffer (pH=6.0) was used as a filling liquid.

This body fluid processor was washed with 2000 ml of physiological saline and using 60 ml of bovine blood (ionized Ca concentration: ca 0.2 mM), which has been subjected to anticoagulation by citric acid, as a blood pool, the blood was circulated through the above body fluid processor at a flow rate of 0.6 ml/min (superficial linear velocity: ca 0.76 cm/min) during the initial 15-minute period and, thereafter, at a flow rate of 1.6 ml/min (superficial liner velocity: ca 2.0 cm/min). As a result, passage of the blood cell was satisfactory and a stable blood circulation could be obtained. The passage ratios of various blood cells were shown in Table 1.

Comparative Example 3

Of the particles for processing body fluid prepared in Example 1, 15.5 ml, 16.4 ml, and 17.9 ml, all in sedimentation volume, were taken and packed into vessels similar to those used in Example 4 to prepare body fluid processors with packing ratios of ca 104%, ca 110% and ca 120%, respectively, and a uniform occupancy ratio of more than 100%. Physiological saline was used as a filling liquid.

Bovine blood was circulated through these body fluid processors in the same manner as in Example 4. As a result, passage of the platelet was invariably unstable and column plugging took place, preventing continuation of circulation after 60 minutes. The passage ratios of various blood cells were shown in Table 1.

Example 5

Of the particles for processing body fluid prepared in Example 1, 11.9 ml in sedimentation volume was taken and packed into a 1 cm (in. dia.) cylindrical vessel (the volume of packed zone: ca 12.7 ml) equipped with two 50 μm-apertured polyester meshes rigidly mounted at a mesh-to-mesh distance of 16.2 cm to prepare a body fluid processor with a packing ratio of ca 94% and an occupancy ratio of ca 100%. Physiological saline was used as a filling liquid.

Through this body fluid processor, human blood treated with 10 volume % to the blood of the anticoagulant ACD-A solution was passed at a flow rate of 1.2 ml/min (superficial linear velocity: ca 1.5 cm/min) in a one-pass mode. As a result, passage of the blood cell was satisfactory and a stable blood perfusion could be obtained. The passage ratios of various blood cells were shown in Table 1.

Comparative Example 4

Of the particles for processing body fluid prepared in Example 1, 14.0 ml and 15.2 ml, both in sedimentation volume, were respectively taken and packed into a vessel similar to the one used in Example 5 to prepare body fluid processors with packing ratios of ca 110% and ca 126%, respectively, and a uniform occupancy ratio of more than 100%. Physiological saline was used as a filling liquid.

When human blood was passed in the same manner as in Example 5, passage of the platelet was unstable, preventing circulation of blood in about 30 minutes with both processors. The passage ratios of various blood cells were shown in Table 1.

Example 6

Except that porous cellulose beads with a mean particle diameter of about 270 μm were used in lieu of the porous cellulose beads with a mean particle diameter of 190 μm, the procedure described in Example 1 was repeated to prepare the particles for processing body fluid.

Of the above particles for processing body fluid, 13.9 ml in sedimentation volume was taken and packed into a vessel similar to the one used in Example 4 to prepare a body fluid processor with a packing ratio of ca 93% and an occupancy ratio of ca 100%. Physiological saline was used as a filling liquid.

Using 70 ml of human blood treated with 10 volume % to the blood of the anticoagulant ACD-A solution as a blood pool, the blood was circulated through the above body fluid processor at a flow rate of 0.6 ml/min (superficial linear velocity: ca 0.76 cm/min) during the initial 15-min period and a flow rate of 1.6 ml/min (superficial linear velocity: ca 2.0 cm/min) thereafter. As a result, passage of the blood cell was satisfactory and a stable blood perfusion could be obtained. The passage ratios of various blood cells were shown in Table 1.

Furthermore, this body fluid processor was found to efficiently adsorb low-density lipoprotein-cholesterol (LDL-C) and triglyceride (TG).

|  | Before blood perfusion | After blood perfusion |
| --- | --- | --- |
| LDL-C concentration of blood pool (mg/dl-plasma) | 88 | 20 |
| TG concentration of blood pool (mg/dl-plasma) | 110 | 57 |

TABLE 1

| | Conditions of blood perfusion | Packing ratio [%] | Occupancy ratio [%] | | Passage ratio of blood cells [%] | | |
|---|---|---|---|---|---|---|---|
| | | | | | 30 minutes | 60 minutes | 90 minutes |
| Example 1 | Bovine blood/ circulation | 97 | 100 | Erythrocyte | 97 | 101 | 101 |
| | | | | Leukocyte | 96 | 89 | 86 |
| | | | | Platelet | 86 | 87 | 86 |
| Example 2 | Bovine blood/ circulation | 100 | 100 | Erythrocyte | 104 | 98 | 98 |
| | | | | Leukocyte | 98 | 93 | 91 |
| | | | | Platelet | 89 | 117 | 93 |
| Example 3 | Bovine blood/ circulation | 97 | 100 | Erythrocyte | 112 | 92 | 100 |
| | | | | Leukocyte | 101 | 80 | 80 |
| | | | | Platelet | 110 | 93 | 107 |
| Example 4 | Bovine blood/ circulation | 90 | 100 | Erythrocyte | 108 | 91 | 89 |
| | | | | Leukocyte | 102 | 99 | 101 |
| | | | | Platelet | 112 | 102 | 94 |
| Example 5 | Human blood/ one-pass | 94 | 100 | Erythrocyte | 100 | Not performed | Not performed |
| | | | | Leukocyte | 100 | Not performed | Not performed |
| | | | | Platelet | 97 | Not performed | Not performed |
| Example 6 | Human blood/ circulation | 93 | 100 | Erythrocyte | 100 | 100 | 100 |
| | | | | Leukocyte | 99 | 99 | 100 |
| | | | | Platelet | 99 | 94 | 101 |
| Comparative Example 1 | Bovine blood/ circulation | 103 | more than 100 | Erythrocyte | 101 | 97 | 93 |
| | | | | Leukocyte | 95 | 86 | 68 |
| | | | | Platelet | 58 | 61 | 2 |
| Comparative Example 2 | Bovine blood/ circulation | 107 | more than 100 | Erythrocyte | 98 | Passage infeasible | Passage infeasible |
| | | | | Leukocyte | 67 | Passage infeasible | Passage infeasible |
| | | | | Platelet | 11 | Passage infeasible | Passage infeasible |
| Comparative Example 3-1 | Bovine blood/ circulation | 104 | more than 100 | Erythrocyte | 76 | Passage infeasible | Passage infeasible |
| | | | | Leukocyte | 99 | Passage infeasible | Passage infeasible |
| | | | | Platelet | 12 | Passage infeasible | Passage infeasible |
| 3-2 | Bovine blood/ circulation | 110 | more than 100 | Erythrocyte | 75 | 58 | Passage infeasible |
| | | | | Leukocyte | 99 | 89 | Passage infeasible |
| | | | | Platelet | 43 | 26 | Passage infeasible |
| 3-3 | Bovine blood/ circulation | 120 | more than 100 | Erythrocyte | 81 | Passage infeasible | Passage infeasible |
| | | | | Leukocyte | 95 | Passage infeasible | Passage infeasible |
| | | | | Platelet | 19 | Passage infeasible | Passage infeasible |
| Comparative Example 4-1 | Human blood/ one-pass | 110 | more than 100 | Erythrocyte | 96 | Not performed | Not performed |
| | | | | Leukocyte | 100 | Not performed | Not performed |
| | | | | Platelet | 9 | Not performed | Not performed |
| 4-2 | Human blood/ one-pass | 126 | more than 100 | Erythrocyte | 97 | Not performed | Not performed |
| | | | | Leukocyte | 100 | Not performed | Not performed |
| | | | | Platelet | 36 | Not performed | Not performed |

Example 7

Of the particles for processing body fluid prepared in Example 1, 640 ml and 654 ml, both in sedimentation volume, were taken and packed into vessels similar to those used in Example 3 to prepare two body fluid processors with packing ratios of ca 88% and ca 90%, respectively, and a uniform occupancy ratio of ca 100%. Citric acid-sodium citrate buffer solution (pH=6.0) was used as a filling liquid.

Each of these body fluid processors was packaged with a suitable cushioning material, accommodated in a box, and as a simulation of commercial shipment and storage, vibrated in horizontal and vertical directions for 1 hour each in accordance with JIS Z0232 "Methods for Vibration Test of Packaged Articles for Transportation and Containers". From the body fluid processor after vibration, the particles for processing body fluid were flushed out with a microparticle-free liquid to withdraw the entirety of the particles together with the filling liquid in the slurry form into a recovery vessel. This slurry was shaken to separate the microparticles from the particles for processing body fluid and allowed to stand for 3 minutes. Then, 2 ml of the supernatant was taken and analyzed for the concentration of the microparticles in the supernatant. This microparticle concentration was multiplied by the volume of the liquid phase of the slurry to find the number of microparticles in the body fluid processor. As a result, the number of microparticles measuring not less than 10 μm but less than about 50 μm in diameter was 4904 on the average and the number of microparticles measuring not less than 25 μm but less than about 50 μm in diameter was 455 on the average. For determination of the concentration of microparticles, a Coulter Counter of the electric resistance type was used and as the aperture tube, a 100 μm tube was used.

Example 8

Of the particles for processing body fluid prepared in Example 1, 655 ml in sedimentation volume was taken and packed into a vessel similar to the one used in Example 3 to prepare a body fluid processor with a packing ratio of ca 90% and an occupancy ratio of ca 100%. Citric acid-sodium citrate buffer solution (pH=6.0) was used as a filling liquid.

This body fluid processor was vibrated in the same manner as in Example 7. Using the body fluid processor after vibration, the number of microparticles flushed out of the body fluid processor was counted by the following method taking the practical setting into consideration.

Physiological saline for injection was delivered into the body fluid processor at a flow rate of 100 ml/min (superficial linear velocity: ca 2.6 cm/min) for 2 hours and test fluid samples flowing out of the body fluid processor were collected immediately after passage and at 0.5 hr, 1 hr, 1.5 hr, and 2 hr. In parallel, physiological saline for injection was sampled as a blank test. Using a Coulter counter, the number of microparticles in each of the test samples and blank test samples was counted and the difference in the number of microparticles between the test sample and the blank test sample was taken as the number of generated microparticles. Determination of the number of the microparticles from the body fluid processor revealed no microparticles.

Example 9

A commercial cellulose acetate was dissolved in a solvent mixture of dimethyl sulfoxide and propylene glycol and this solution was made into droplets and coagulated by the method described in Japanese Kokai Publication Sho-63-117039 (vibration method) to prepare cellulose acetate beads. The beads were mixed with an aqueous solution of sodium hydroxide for hydrolysis to give cellulose beads. The mean particle diameter of the cellulose beads was 460 µm.

After a sufficient quantity of water was added to 1700 ml of the epoxy-activated cellulose beads to make 3400 ml, 900 ml of 2 M aqueous sodium hydroxide solution was added and the temperature was adjusted to 40° C. To this mixture was added 310 ml of chloromethyloxysilane, and the reaction was carried out under stirring at 40° C. for 2 hours. After completion of the reaction, the beads were thoroughly rinsed with water to give epoxy-activated cellulose beads.

To 1000 ml of the above epoxy-activated cellulose beads was added 20 g of n-hexadecylamine, and the reaction was conducted in 50 (v/v) % ethanol/water under standing at 45° C. for 6 days. After completion of the reaction, the beads were serially washed well with 50 (v/v) % ethanol/water, ethanol, 50 (v/v) % ethanol/water, and water to give n-hexadecylamine-coupled cellulose beads (the particles for processing body fluid).

Of the above the particles for processing body fluid, 300 ml and 330 ml, both in sedimentation volume, were respectively taken and packed into 7.0 cm (in. dia.) cylindrical vessels (the volume of packed zone: ca 350 ml) each equipped with two 150 µm-apertured polyester meshes rigidly mounted at a mesh-to-mesh distance of 9.1 cm to prepare body fluid processors with packing ratios of ca 86% and ca 94%, respectively, and a uniform occupancy ratio of ca 98.9%. Citric acid-sodium citrate buffer (pH=6.0) was used as a filling liquid.

These body fluid processors were vibrated in the same manner as in Example 7 and the number of microparticles in each body fluid processor was determined. As a result, the number of microparticles measuring not less than 10 µm but less than about 50 µm in diameter was 4851 on the average and the number of microparticles measuring not less than 25 µm but less than about 50 µm in diameter was 139 on the average.

Comparative Example 5

Of the body fluid particles prepared in Example 9, 300 ml and 335 ml, both in sedimentation volume, were respectively taken and packed into vessels similar to those used in Example 9 to prepare body fluid processors with packing ratios of ca 87% and ca 94%, respectively, and a uniform occupancy ratio of ca 94%. Citric acid-sodium citrate buffer solution (pH=6.0) was used as a filling liquid.

These body fluid processors were vibrated in the same manner as in Example 7 and the number of microparticles in each body fluid processor was determined. As a result, the number of microparticles measuring not less than 10 µm but less than about 50 µm in diameter was 40589 on the average and the number of microparticles measuring not less than 25 µm but less than about 50 µm in diameter was 2622 on the average.

Example 10

Except that porous cellulose beads with a mean particle diameter of ca 240 µm was used in lieu of the porous cellulose beads with a mean particle diameter of ca 190 µm, the procedure described in Example 1 was repeated to prepare the particles for processing body fluid.

Of the above the particles for processing body fluid, 708 ml in sedimentation volume was taken and packed into a 7 cm (in. dia.) cylindrical vessel equipped with two 48 µm-apertured polyester meshes rigidly mounted at a mesh-to-mesh distance of 19.8 cm (the volume of packed zone: ca 760 ml) to prepare a body fluid processor with a packing ratio of ca 93% and an occupancy ratio of ca 98%. Citric acid-sodium citrate buffer solution (pH=6.0) was used as a filling liquid.

This body fluid processor was vibrated and the number of microparticles in the body fluid processor was counted in the same manner as in Example 7. As a result, the number of microparticles measuring not less than 10 µm but less than ca 50 µm in diameter was 6638 on the average and the number of microparticles measuring not less than 25 µm but less than ca 50 µm was 1021 on the average.

INDUSTRIAL APPLICABILITY

In accordance with the present invention there can be provided a safe and practically useful body fluid processor enabling direct hemoperfusion with a favorable passage of the blood cell and showing an extremely low risks of the generation and leakage of microparticles. Furthermore, as a body fluid processor enabling direct hemoperfusion is thus provided, the burden on the patient and medical staff can be reduced through, for example, a curtailed treatment session time.

The invention claimed is:

1. A body fluid processor enabling direct hemoperfusion, which comprises a vessel equipped with a fluid inlet, a fluid outlet and a mesh attached adjacent to said fluid outlet, said vessel being packed with particles for processing body fluid and a filling liquid, and said body fluid processor having a packing ratio of 85 to 100% and the space in which the particles for processing body fluid are to be packed in the body fluid processor being filled with the particles for processing body fluid and said filling liquid at a ratio of 95% or more but not more than 100%, wherein said packing ratio is a value calculated by means of the following equation:

Packing ratio (%)=$Va/Vj \times 100$ where Va represents a sedimentation volume of the particles for processing body fluid packed in the space in which the particles for processing body fluid are to be packed and Vj represents the volume of the space in which the particles for processing body fluid are to be packed, and wherein the mean particle diameter of the particles for processing body fluid is 80 μm through 500 μm and the aperture size of the mesh is not less than 20 μm but less than ½ of the mean particle diameter of the particles for processing body fluid.

2. The body fluid processor enabling direct hemoperfusion according to claim 1, wherein the particles for processing body fluid are hard particles.

3. The body fluid processor enabling direct hemoperfusion according to claim 1, wherein a carrier for the particles for processing body fluid is a hydrophilic carrier.

4. The body fluid processor enabling direct hemoperfusion according to claim 1, wherein a carrier for the particles for processing body fluid is a carrier made of a cellulosic material.

* * * * *